(12) United States Patent
Martikka et al.

(10) Patent No.: US 11,856,342 B2
(45) Date of Patent: Dec. 26, 2023

(54) ARRANGEMENT AND METHOD FOR CONFIGURING EQUIPMENT

(71) Applicant: Suunto Oy, Vantaa (FI)

(72) Inventors: Mikko Martikka, Vantaa (FI); Kimmo Pernu, Vantaa (FI); Erik Lindman, Vantaa (FI); Terho Lahtinen, Vantaa (FI)

(73) Assignee: Suunto Oy, Vantaa (FI)

( * ) Notice: Subject to any disclaimer, the term of this patent is extended or adjusted under 35 U.S.C. 154(b) by 332 days.

(21) Appl. No.: 15/263,401

(22) Filed: Sep. 13, 2016

(65) Prior Publication Data

US 2016/0375305 A1 Dec. 29, 2016

Related U.S. Application Data

(60) Division of application No. 15/189,051, filed on Jun. 22, 2016, which is a continuation-in-part of application No. 14/585,255, filed on Dec. 30, 2014.

(30) Foreign Application Priority Data

Dec. 31, 2013 (FI) ...................................... 20136346

(51) Int. Cl.
*H04Q 9/00* (2006.01)
*A41B 1/00* (2006.01)
(Continued)

(52) U.S. Cl.
CPC ................ *H04Q 9/00* (2013.01); *A41B 1/00* (2013.01); *A41D 1/002* (2013.01); *A41D 1/06* (2013.01);
(Continued)

(58) Field of Classification Search
CPC ...... A63B 24/0062; A63B 71/06; H04Q 9/00; H04Q 2209/43
(Continued)

(56) References Cited

U.S. PATENT DOCUMENTS 4,583,547 A 4/1986 Granek et al.
6,266,774 B1 7/2001 Sampath et al.
(Continued)

FOREIGN PATENT DOCUMENTS

EP 1531726 B1 12/2009
EP 2779003 A2 9/2014
(Continued)

*Primary Examiner* — Kam Wan Ma
(74) *Attorney, Agent, or Firm* — Laine IP Oy

(57) ABSTRACT

The invention concerns an arrangement and a method for configuring equipment for personal performance monitoring comprising at least one carrier item having a mounting zone for receiving a communication module, one or more sensors and/or actuators and a first processing unit functionally connected to said mounting zone and said sensors and/or actuators. The first processing unit is configured to process sensor signals from the sensors and/or actuators and to communicate with a communication module that is mounted on the mounting zone of the carrier item and having a second processing unit configured to further process said sensor/actuator signals and to communicate processed signals to a remote device over a wireless communication protocol. A remote device is adapted to provide a predefined code to configure the equipment to process sensor or actuator signals according to a use of said carrier item as identified by said predefined code.

19 Claims, 8 Drawing Sheets

(51) Int. Cl.

| | | |
|---|---|---|
| *A41D 1/06* | (2006.01) | |
| *A43B 3/34* | (2022.01) | |
| *A63B 60/46* | (2015.01) | |
| *A41D 1/00* | (2018.01) | |
| *A41F 9/00* | (2006.01) | |
| *A43B 5/00* | (2022.01) | |
| *A61B 5/11* | (2006.01) | |
| *A61B 5/00* | (2006.01) | |
| *A63B 24/00* | (2006.01) | |
| *B62J 45/412* | (2020.01) | |
| *B62J 45/414* | (2020.01) | |
| *B62J 45/42* | (2020.01) | |
| *A63C 11/00* | (2006.01) | |

(52) U.S. Cl.
CPC .................. *A41F 9/00* (2013.01); *A43B 3/34* (2022.01); *A43B 5/00* (2013.01); *A61B 5/11* (2013.01); *A61B 5/6804* (2013.01); *A61B 5/6807* (2013.01); *A63B 24/0062* (2013.01); *A63B 60/46* (2015.10); *A41D 2600/10* (2013.01); *A63B 2024/0065* (2013.01); *A63B 2220/12* (2013.01); *A63B 2220/30* (2013.01); *A63B 2220/40* (2013.01); *A63B 2220/50* (2013.01); *A63B 2225/54* (2013.01); *A63B 2230/60* (2013.01); *A63C 11/00* (2013.01); *B62J 45/412* (2020.02); *B62J 45/414* (2020.02); *B62J 45/42* (2020.02); *H04Q 2209/43* (2013.01); *H04Q 2209/86* (2013.01)

(58) Field of Classification Search
USPC .................................................. 340/870.07
See application file for complete search history.

(56) References Cited

U.S. PATENT DOCUMENTS

| | | | |
|---|---|---|---|
| 6,675,201 | B1 | 1/2004 | Parkkinen |
| 7,698,101 | B2 | 4/2010 | Alten et al. |
| 8,253,586 | B1 | 8/2012 | Matak |
| 8,933,801 | B2 | 1/2015 | Sweeney et al. |
| 9,595,187 | B2 | 3/2017 | Kotz et al. |
| 9,788,138 | B2 | 10/2017 | Miller |
| 2004/0045000 | A1 | 3/2004 | Hara |
| 2005/0176461 | A1 | 8/2005 | Bozzone et al. |
| 2005/0192129 | A1 | 9/2005 | Kuwabara |
| 2005/0278194 | A1 | 12/2005 | Holland et al. |
| 2006/0143645 | A1 | 6/2006 | Vock et al. |
| 2008/0076972 | A1 | 3/2008 | Dorogusker et al. |
| 2008/0096726 | A1 | 4/2008 | Riley |
| 2008/0125288 | A1 | 5/2008 | Case |
| 2008/0133265 | A1 | 6/2008 | Silkaitis et al. |
| 2008/0319330 | A1 | 12/2008 | Juntunen et al. |
| 2009/0195350 | A1 | 8/2009 | Tsern et al. |
| 2011/0010704 | A1 | 1/2011 | Jeon et al. |
| 2011/0060812 | A1 | 3/2011 | Middleton |
| 2011/0152695 | A1 | 6/2011 | Granqvist et al. |
| 2011/0221590 | A1 | 9/2011 | Baker et al. |
| 2012/0136231 | A1 | 5/2012 | Markel |
| 2012/0252544 | A1* | 10/2012 | Yuen ...................... G06F 3/011 455/575.8 |
| 2013/0096704 | A1 | 4/2013 | Case, Jr. |
| 2013/0203518 | A1 | 8/2013 | Hatton et al. |
| 2013/0267339 | A1 | 10/2013 | Boyd et al. |
| 2013/0274587 | A1 | 10/2013 | Coza et al. |
| 2013/0307675 | A1 | 11/2013 | Teng |
| 2014/0172134 | A1 | 6/2014 | Meschter |
| 2014/0278125 | A1 | 9/2014 | Balakrishnan et al. |
| 2014/0330408 | A1 | 11/2014 | Rolley |
| 2014/0361875 | A1 | 12/2014 | O'Hagan et al. |
| 2015/0182841 | A1* | 7/2015 | Martikka ............... A63B 71/06 340/870.07 |
| 2015/0182842 | A1 | 7/2015 | Martikka et al. |
| 2016/0303426 | A1* | 10/2016 | Martikka ............... A63B 60/46 |

FOREIGN PATENT DOCUMENTS

| | | |
|---|---|---|
| WO | WO2009097591 A1 | 8/2009 |
| WO | WO2010016025 A1 | 2/2010 |
| WO | WO2013096954 A1 | 6/2013 |

* cited by examiner

ARRANGEMENT AND METHOD FOR CONFIGURING EQUIPMENT

FIELD OF THE INVENTION

The invention relates to systems used for personal performance monitoring for example in sports. In particular, the invention relates to a novel configuration arrangement and method for equipment that includes communication modules for communicating sensor signals, such as EMG signals.

BACKGROUND OF THE INVENTION

It is well known to measure electromyographic (EMG) signals from different parts of a human body during e.g sports performances, the most common example being heart beat measurement using a surface EMG sensor-containing heart beat belt with a wireless transmitter module for communicating with a personal monitoring device, such as a sports watch. Measurement of surface EMG signals also from other parts of the body to monitor muscle activity in legs, arms, middle body or torso, for example. Such measurements can be carried using EMG sensors for example integrated into sports garment. It is also known to integrate signal transmitter modules into the belt or garment or to provide the module as a snap-on module to an assembly zone on the garment or belt. The module can be removed for washing the garment, for example. One disadvantage in known systems is that, although the transmitter can be removable and reconnectable, each sensor or sensor group requires a specifically designed transmitter module in order to operate properly.

To mention some specific examples, U.S. Pat. No. 8,253,586 discloses a performance measuring system comprising an article of clothing with an integrated measuring sensor and additionally a communication module, power module and computing module attachable to the article of clothing. The modules can be removed from one article of clothing and used in another article of clothing, while the sensor remains in the article. EP 1531726 discloses the use of a multitude of surface EMG electrodes to gain information simultaneously from muscles in various parts of the body. Also U.S. Pat. No. 4583547 relates to a similar application and in particular how conductive paths in garment can be arranged to provide a sensor signal form the measurement point to the signal transmitter module.

US 2008/0319330 discloses as a further example of currently available techniques a mobile transmitter for observing performance-related events and transmitting data on the observed events to a receiver. The transmitter comprises a timer for providing time references relating to the events and a memory for recording time references. The transmitter obtains a time reference from the timer and records the obtained time reference in the memory and is adapted to produce data messages containing a predetermined number of time references obtained from the memory and further to transmit the produced data messages to the receiver. The disclosed system allows for time stamping of events, such as heartbeats, and calculating the frequency and/or interval variation parameters of heartbeats. The system does not allow for synchronizing events from different detector sources.

U.S. Pat. No. 7,698,101, on the other hand, discloses a system for pairing sensor-containing shoes with measurement electronics, including authentication of the shoes for the electronics. Also these solutions require dedicated transmitter module sensor pairs in order to be able to transmit the measurement signal to a monitoring unit. US 2013/0096704 discusses articles of clothing and module capable of sensing physical and/or physiological characteristics associated with the use of the clothing. The module contains one or more integral sensors. The system can activate the module or sensor in it upon engaging the module to the clothing and confirm that the clothing and the module are authorized for use with one another and/or for automatic data processing algorithm selection. The flexibility of the system is, however, restricted to adaptation of the sensor module to use its built-in sensor(s) in different ways depending on the clothing it is attached to. Thus, several modules are still needed or a single module needs to be equipped with a plurality of sensors if different types of signals are to be measured.

One problem also touched by the abovementioned publications in a multi-sensor system is the communication of the different EMG measurement signals to a monitoring device. There are systems, which utilize wired communication channels from a plurality of sensors to a single module. Such systems become impractical if there is a need to use many sensors at distant body parts and potentially separate belt or garment units.

Thus, there exists a need for generic solutions for facilitating configuration and communication between sports and other carrier items, such as EMG sensor-containing garment or a tool, and a remote monitoring unit.

SUMMARY OF THE INVENTION

It is an aim of the invention to solve at least some of the abovementioned problems and to provide an arrangement and method for configuring equipment for performance monitoring and/or facilitation, which allows for configuration between different kinds of carrier items in a modular equipment system with the aid of remote monitoring unit.

The invention is based on the general idea of arranging a data processing and communication link between a carrier item and a central monitoring unit in a novel way. In focus of the invention, there is a communication module, which is capable of distinguishing the place of mounting thereof so that it may adapt its internal operation accordingly. For example, in a sports system or arrangement comprising a communication module and a sports item, the sports item comprises a mounting zone capable of indicating its identifier to the communication module once the module being mounted thereon.

In more detail, to meet the abovementioned aims, the invention provides in some embodiments an arrangement for configuring sports equipment for personal performance monitoring and/or facilitation. The sports equipment comprises at least one sports item, at least one communication module and a remote device. The sports item comprises a mounting zone for receiving a communication module, one or more sensors and/or actuators, a first processing unit functionally connected to said mounting zone and said sensors and/or actuators and configured to process sensor signals from said sensors and/or actuators and to communicate with a communication module. The communication module is adapted to be mounted on said mounting zone of the sports item and having a second processing unit configured to further process said sensor/actuator signals and to communicate processed signals to a remote device over a wireless communication protocol. The remote device is adapted to communicate with said communication module over said wireless communication protocol and to send a predefined code to said communication module to configure the same to process sensor or actuator signals from said sports item according to a use of said sports item as identified by said predefined code.

The communication module may be configured to write said predefined code into a first memory unit in order to enable said first and second processing units to process sensor or actuator signals from said sports item according to an instruction set corresponding to said use of said sports item. The instruction set may be fetched from said remote device and stored in a second memory unit in said communication module, or the instruction set may be generated from said code by an algorithm stored in a second memory unit in said communication module. An instruction set is a "motion recipe" for how to interpret the sensor signals according to a sport or activity the recipe has been designed for.

The first memory unit may reside in the sports item, whereby it is functionally connected to said first processing unit, or it may reside in the communication module and may be functionally connected to either the first or said second processing unit, or both.

According to some embodiments, the invention provides an arrangement for configuring sports equipment for personal performance monitoring and/or facilitation. The sports equipment comprises at least one sports item, at least one communication module and a remote device. The sports item comprises a mounting zone for receiving a communication module, one or more sensors and/or actuators, a tag comprising a near-field antenna and a first memory unit, and a first processing unit functionally connected to said mounting zone, said sensors and/or actuators and said tag. The first processing unit is configured to process sensor signals from said sensors and/or actuators and to communicate with a communication module. The tag in the sports item may comprise a radio-frequency identification (RFID) unit.

The communication module is adapted to be mounted on said mounting zone of the sports item and has a second processing unit configured to further process said sensor/actuator signals and to communicate processed signals to a remote device over a wireless communication protocol. The remote device is adapted to communicate with said tag in the sports item over a near-field communication protocol in order to write a predefined code into said first memory unit and to configure said sports item to process sensor or actuator signals from said sports item together with said communication module according to a use of said sports item as identified by said predefined code.

The sports item may be configurable by the predefined code to enable said first and second processing units to process sensor or actuator signals from said sports item according to an instruction set corresponding to said use of said sports item. The instruction set may be fetched from said remote device and stored in a second memory unit in said communication module, or it may be generated from said code by an algorithm stored in a second memory unit in said communication module. The ID code need not necessarily contain just an identifier, like an electronic product code (EPC), but may also contain variable information and code sequences which enables the communication module to configure itself and the sports item according to the intended use and to create an instruction set to this effect.

The remote device may have access to a plurality of instructions sets corresponding to different predefined uses of said sports item. Such access may be provided by internet to a service provider hosting such instruction sets, for example. The remote device may be a smart phone or the like with an application running to facilitate the access.

In some embodiments of the invention, the sports items may comprise a belt, a garment and/or a piece of sports equipment, such as a bat, racket, club, ski or bicycle, with one or more integrated sensors or actuators. The sensors or actuators may be EMG sensors, acceleration sensors, power sensors, speed sensors, a satellite positioning sensor or a trigger actuator for a trigger or drive signal.

In some embodiments of the invention, the mounting zone for the communication module comprise conductive fasteners such as snaps located on an outer surface of a housing for said communication module, in order to secure the communication module to the mounting zone and for providing electronic contact terminals for communication between said sports item and said communication module.

According to some embodiments of the invention, an arrangement and a method for configuring a tool in order to monitor personal performance, when working with such tool, is provided.

More specifically, the inventive arrangement and method is defined in the independent claims.

The invention has considerable advantages. Importantly, the invention allows for a single communication module to be used together with a variety of different peripheral devices, most notably sensors and actuators herein discussed. The functions of the device are determined only once attached to the item containing the sensor or actuator, by reading an identifier of the item and self-adapting the module according to the identifier.

The invention significantly improves modularity of existing sports monitoring or facilitation systems. By means of the invention, a single generic communication module can be used with sports garment and other sports items designed for particular sports. For example, the same module can be used during one training session in a heart rate belt for heart rate signal processing and transmission and in another sessions attached to muscle EMG sensor-containing clothing for muscle activity detection and activity signal transmission, or even a foot pod or bicycle pod for speed signal processing and transmission, to mention a completely different kind of measurement. By means of the invention, it is also convenient to build distributed performance monitoring systems with sensors grouped in suitable single-sensor units and/or multi-sensor groups each serving for a particular purpose and associated with a single communications module. Although the system is distributed, the amount of physical wiring can be kept reasonable because of wireless communication between the communication modules and the monitoring unit.

Long wires as used in prior art solutions are sensitive to interference, as the EMG voltages are low. With the aid of the invention, robust data transfer between the measuring points and a monitoring unit can be established. Only the wires between the sensors or actuators and the distributed mounting zones need to be integrated to the garments, for example.

The invention can be used with any sports items within a personal-area network of a person. This includes at least all items that the person wears, holds or touches during the performance.

Adaptivity of the module can be implemented in a variety of ways, including choosing suitable processing instructions from a set of processing instructions pre-stored in the module, over a two-way data communication channel with a monitoring unit carried by the user, over a two-way data communication channel with a computer, or over a two-way internet data communication channel (cloud service).

DEPENDENT CLAIMS FOCUS ON SELECTED EMBODIMENTS OF THE INVENTION

According to one embodiment, there is provided a communication module comprising conductive means for mounting the communication module to a mounting zone on a carrier item, the conductive means forming both physical mounting points and electronic contact terminals for making an electronic contact with the carrier item while being mounted thereon.

According to one embodiment, the wireless communication unit of the module is capable of transmitting data received through the contact terminals and processed in the module to a remote monitoring device. This allows the module to be used with sensor-containing carrier items.

According to one embodiment, the wireless communication unit is capable of both sending data to and receiving data from the remote monitoring device. This embodiment further allows receiving processing instructions not initially stored in the memory of the module, extending the range of use of the module greatly.

According to one embodiment, the processing unit of the module is functionally connected to said contact terminals and to said wireless communication unit and capable of processing data received through the contact terminals and for storage and/or transmission of the processed data through the wireless communication unit according to data processing instructions contained in memory thereof. According to a further embodiment, the processing unit is capable of processing data received through the wireless communication unit and transmitting the data through the contact terminals. Thus, either one- or two-way communication, and optional intermediate data processing, between the wireless communication unit and the contact terminals is possible.

According to one embodiment, the communication module comprises means for reading an electronic identifier in the form of a data field in a first electronic memory device contained in the sports item and accessible by the module.

According to one embodiment, the means for reading the identifier from the carrier item are adapted to read the identifier from the electronic memory device over a wired connection through the contact terminals. Thus, no separate connectors for reading the identifier are needed in the module. Alternatively, the means for reading the identifier comprise wireless transceiver unit, such as a radio-frequency identification (RFID) unit, for reading the identifier from a carrier item equipped with a corresponding transponder containing the electronic memory device. This embodiment requires more additional electronics in the module but allows for contactless reading of the identifier and spares the contact terminals of sensor/actuator communication use only.

Both the communication and data processing characteristics of the processing unit are capable of being changed by operating environment-specific reprogramming of the processing unit, i.e., by changing the internal data processing instructions of the processing unit based on the identifier read.

According to one embodiment, the module comprises an second memory for storing a set of data processing instructions corresponding to different identifiers and the processing unit is capable of choosing the data processing instructions from said set of data processing instructions based on the value of the identifier read. Alternatively or in addition, a desired instruction set may be generated and stored in the second memory by an algorithm, which is processed by the module based on an identifier read from a carrier item.

This embodiment allows for a set of instructions for example corresponding to identifiers of most common carrier items, such as a heart rate belt and selected pieces of muscle activity sensor garment, or various tools.

Alternatively or in addition to containing an internally stored set of instructions, the processing unit may capable of sending a request for data processing instructions corresponding to the value of the identifier read and receiving said data processing instructions through said wireless communication unit to/from an external wireless device, preferably said monitoring unit, and optionally storing the received data processing instructions in the set of data processing instructions in the second memory for also further use. This embodiment extends the use of the module to all kinds of applications not even known at the moment of release of the module.

To implement a typical use involving sensor co-operation with the module, the processing unit is capable of receiving a sensor signal from the carrier item through the contact terminals and processing the sensor signal according to the data processing instructions chosen to provide processed sensor data. Further, the processing unit is adapted to transmit the processed sensor data to the monitoring device through the wireless communication unit. The following sensor signals may be supported, for example: EMG signal from an EMG sensor, acceleration signal from an acceleration sensor, power signal from a power sensor, speed signal from a speed sensor, position signal from a satellite positioning sensor, pressure signal form a pressure sensor. Further uses are discussed elsewhere in the document. It should be noted that in the software level, the changeable processing instructions of the processing unit determine the operation of the processing unit, but the module must be designed in the hardware and firmware levels to enable such functionalities.

According to another main use of the module, the processing unit is capable of receiving actuation data from the monitoring device through the wireless communication unit, processing the actuation data according to the data processing instructions chosen to provide an actuation signal, and transmitting the actuation signal to the sports item through the contact terminals according to the data processing instructions. This kind of actuator co-operation (or "facilitation" use) is roughly inverse to the sensor co-operation. The actuation signal may be a power signal, trigger signal or display drive signal, for example, or any combination thereof. Again the module must be designed in the hardware and firmware levels to enable such functionalities upon suitable reprogramming in the software level. I.e., there must be some power output capacity in the module for allowing carrier items without internal power supplies to be used.

According to one embodiment, the module comprises a sensor of some kind, such as an acceleration sensor, functionally connected to the processing unit and a memory with data processing instructions for processing sensor data received from the sensor. This embodiment allows the module to be used also in a stand-alone mode to detect for example acceleration changes. Thus, the module can be used for example as a step detector (foot pod) with ordinary shoes or with shoes only containing a physical mounting zone for the module.

Apart from the mounting means and contact terminals of the module, all other key parts thereof are preferably contained in a housing. In particular, the housing encapsulates the wireless communication unit and the processing unit. The mounting means and the contact terminals are located on outer surface of the housing such that they are easily accessible.

The mounting means and the contact terminals are preferably integrally formed of at least two conductive snap fasteners, such as male or female snap fasteners, being capable of engaging with corresponding conductive counterparts on the carrier item so as to attach the module to the carrier item and to form said electric contact between the module and the carrier item.

According to one embodiment, the present carrier item may comprise a mounting zone for the communication module, the mounting zone comprising two or more second electronic contact terminals for making an electronic contact with the first electronic contact terminals of the communication module according to the invention when mounted to the mounting zone. The mounting zone may comprise e.g. female or male snap fasteners designed to engage corresponding parts of the module described above. Embedded in the carrier item, there may be a first memory unit for storing an identifier of the carrier item, the memory unit being connected to means for communicating the identifier to the communication module when mounted to the mounting zone. Such means may comprise conductors for contact reading of the memory vie the second contact terminals or a radio-frequency transponder unit for wireless reading. In addition, there are one or more sensors or actuators functionally connected to the second electronic contact terminals so as to be able to transfer electric signals between the one or more sensors or actuators and the communication module via the second contact terminals.

The mounting means of the communication module and the mounting zone of the carrier item are preferably designed to allow for repetitive mounting and removing of the communication module(s) thereto/therefrom. Thus, the module can be removed if a person wants to use the module in another sports item, with another tool, or for example during washing of the sports item or charging or changing of a battery of the module.

Indeed, according to one embodiment, the communication module comprises an electric power source, such as a battery, or a zone for placing a power source adapted to power internal functions of the communication module and to provide power to said electronic contact terminals. The internal functions include in particular operation of the communication unit (radio unit), processing unit and means for reading the identifier.

In one particular embodiment, the number of second electronic contact terminals in the carrier item is two and the terminals are connected both to said first memory unit and to the one or more sensors or actuators. The communication link through corresponding first terminals of the communication module and the second terminals of the sports item is arranged such that signal from/to the memory unit and from the sensor(s)/to the actuator(s) are distinguishable, e.g. by their frequency characteristics, so that both the memory unit and the sensor(s)/actuator(s) are useable.

The carrier item may be sports item like a belt, garment or piece of sports equipment, such as a bat, racket, club, ski or bicycle, with one or more integrated sensors or actuators. The carrier item may also be a tool to be used manually, like welding equipment, an axe or a rifle. Further examples are discussed elsewhere in this document.

The communication module and the carrier item according to the invention is preferably used in a system additionally comprising a monitoring unit capable of wirelessly communicating with the communication module so as to receive sensor data from said one or more sensors or transmit actuation signal to said one or more actuators via said communication module. In such system, the communication module is capable of sending a request for data processing instructions corresponding to the value of the identifier read from the sports item to the monitoring unit and receiving said data processing instructions from the monitoring unit, and the monitoring unit is capable of receiving and processing said request and transmitting said data processing instructions wirelessly to the communication module. Processing of the request may comprise retrieving the data processing instructions from a memory of the monitoring unit and/or further requesting the data processing instructions from an external computer or a cloud service.

According to one embodiment, the carrier item contains, in addition to the sensor or actuator, also analogue and/or digital processing unit, which is capable of processing the sensor data before sending to the contact terminals and further to the communication module, or processing signals intended for the actuator. The processing unit typically comprises a microcontroller embedded in the sports item. This embodiment allows for even more generic communication modules to be used, as part of signal processing or intelligent logic operations can be implemented in the carrier item level, as an integral part and function of the carrier item. Preferably, the processing unit is powered by the communication module but may naturally contain also a separate power source. In particular, there may be sensor signal A/D conversion and processing logic in a sensor-containing sports item. The processing may be located either in the vicinity of the sensor or in the vicinity of the mounting zone for the communication module. In this embodiment, the identifier may be provided for the communication module a memory of the processing unit, whereby any separate memory unit for storing the identifier is not needed. The signal for the contact terminals of the carrier item may contain both the identifier and any additional data from the sensor processed in the integral processing unit. It is also possible to provide a two-way wired communication between the communication module and the integral processing unit of the sports item so that preprocessing instructions, for example, are given for the integral processing unit from the communication module.

According to one embodiment, all communication modules in the system, irrespective of their place of mounting, are similar in their hardware design and the operational differences are achieved solely by reprogramming according to the invention based on the identifiers read form the mounting zones.

According to a further aspect of the invention, there are provided sports pants comprising a plurality of integrated EMG sensors adapted to sense EMG signals from at least two leg muscles, such as frontal and/or back thigh muscles, preferably from both legs. There is also provided one or more mounting zones for communication modules as described above, the mounting zones comprising module-readable identifiers. The EMG sensors are connected to contact terminals contained in the mounting zones by wires integrated to the garment structure. The number of mounting zones is typically one (all sensors connected thereto and their signals processed in a module attached thereto) or two (sensors arranged in two groups and their signals processed separately), but may be also larger (more sensor groups).

Definitions

The term "sports item" covers various pieces of garment and other items used when performing sports. In particular, the term covers personal clothing and other wearable items, such as heart rate belts, and personal sports equipment in direct possession of the person performing the sport. The term also covers other sports items that are at least temporarily in the vicinity of the person during the performance, i.e., can join the personal-area network of a central unit (monitoring unit) of the person. An example of such item is a golf bag. Further examples are given in the detailed description. "Sports" should be taken broadly to cover all kinds of physical activities. The more generic term "carrier item" can be a sports item as described above, or a similar arrangement for other than sports equipment, such as tools.

"Mounting zone" is zone on a carrier item dedicated or at least suitable for a communication module according to the invention. A mounting zone comprises both physical and electronic connection means for the communication module to both remain attached to the carrier item and to be able to electrically communicate with one or more sensors and/or actuators therein.

"ID" or "identifier" in a carrier item is a piece of machine-readable data which indicates the type of the carrier item in particular in respect of number and type(s) of sensor(s) and/or actuator(s) therein for allowing a communication module attached to the mounting zone to utilize them. The identifier can be coded in any suitable machine-readable format encoding a specific value. Therefore, references to the "identifier" can be considered as references to the "value of identifier", where applicable. The identifier can for example be a sequence of characters bit-encoded and stored in a semiconductor memory unit.

"Processing instructions" means a computer-readable instruction set (typically arranged in a single data file) with data content, which can be interpreted by the communication module to change its operation to correspond with the requirements of a sports item with a specific ID. The instructions may have effect for example on sensor signal (input signal) processing characteristics (e.g. amplification characteristics) of the module,
actuator control signal (output signal) processing characteristics,
internal sensor or actuator data processing algorithms,
data interface specifications with a sensor and/or actuator, and/or
wireless data communication characteristics with a monitor unit.

The processing instructions may comprise a set of configuration values (passive instructions), computer-executable code (active instructions), or both, in a suitable data structure, most commonly in one or more data file. Thus, the processing instructions are sports item—specific software configuration files or applications, which can be utilized or run by the operating system (firmware) of the module.

"Monitoring" means receiving information on the performance using one or more sensors in one or more carrier items through one or more communication modules. Monitoring is preferably carried out using a wearable monitoring unit, such as a wristop computer, but may be done also using any other computing device capable of communicating with the one or more communication modules. One option is to use a mobile phone as the monitoring unit.

"Facilitation" means actively providing input to a carrier item through a communication module. Facilitation can be carried out using one or more actuators in one or more carrier items. Activation or control signals for the actuator(s) are provided from or via the communication module(s) and they may originate from the monitoring unit discussed above.

Next, embodiments of the invention and advantages thereof are described in more detail with reference to the attached drawings.

DETAILED DESCRIPTION OF EMBODIMENTS

Figure 1:
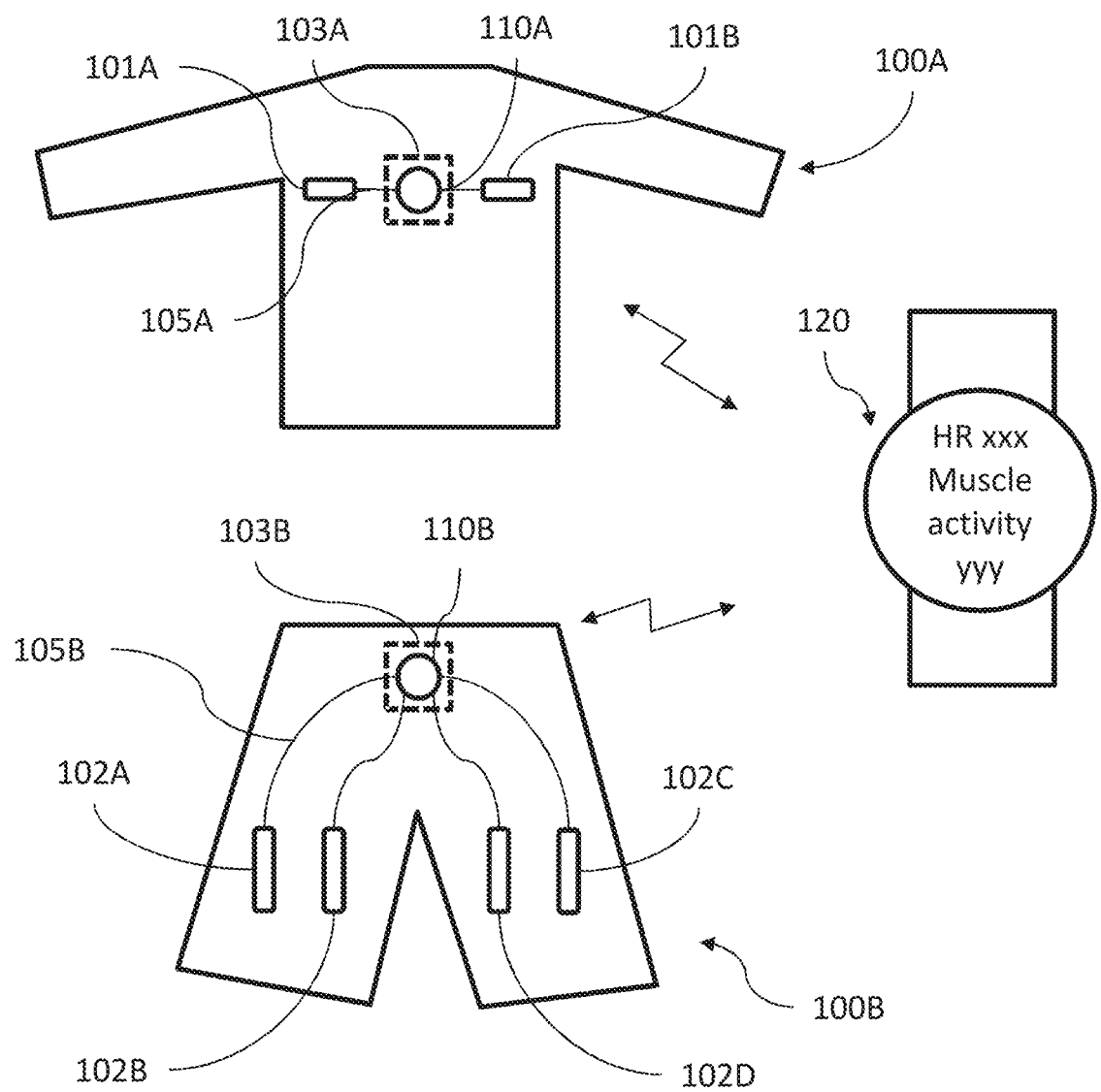
FIG. 1 illustrates a monitoring system according to one embodiment of the invention with communication modules attached to sports garments with integrated EMG sensors.

FIG. 1 shows one example of a sports equipment that can take advantage of the invention. The equipment comprises a first sports garment (shirt) 100A and a second sports garment (shorts) 100B, both containing integrated EMG sensors. The shirt 100A comprises first EMG sensor pads 101A, 101B positioned to measure heart EMG signal. In the shorts 100B, there are second EMG sensor pads 102A-D are positioned in two groups (102A and 102B/102C and 102D) against both thighs to measure thigh muscle EMG activity. The heart EMG pads 101A, 101B are connected to a first mounting zone 103A in the shirt 100A using first wirings 105A. Similarly, the thigh muscle activity EMG pads 102A-D of the shorts 100B are connected to a second mounting zone 103B in the shorts using second wirings 105B.

To the first and second mounting zones 103A, 103B, there are attached a first and a second communication module 110A, 110B, such that they are electrically connected to the first and second wirings 105A, 105B and further to the first and second EMG sensor pads 101A-B, 102A-D, respectively. Both the mounting zones 103A, 103B are identified by identifiers, which may be read by the communication modules 110A, 110B to be able to configure the communication modules for these particular measurement environments. Thus, the modules 110A, 11B can be identical in hardware and firmware but can change their internal operating instructions to co-operate with the environment they are connected to.

A remote unit (wristop computer) 120 is provided, to which the communication modules 110A, 110B wirelessly transmit the measurement information received from the sensors after processing in the processing units of the communication modules 110A, 100B. The remote unit 120 may serve to provide operating instruction sets for the modules 110A, 110B based on the identifiers read by the modules 110A, 110B upon configuration of the modules. Transmitting the instructions may be done through wireless communication. Alternatively, the instruction sets corresponding to the identifiers may be generated in the modules 110A, 110B, whereby no communication with the remote unit 120 at the configuration phase is needed.

To give an example of the configuration of the modules, the identifier of the shirt 100A can "tell" the module 110A that there is one sensor (two pads) of EMG type connected and that the signal amplification level required is X. The identifier of the shorts 100B can "tell" the module 110B that there are two sensors (four pads) both of EMG type connected and that signal amplification level required for both of these is Y. As indicated above, the "telling" may take place through internal-only configuration, where an algorithm for generating the instruction sets is pre-stored in the module, or through communication with the remote, and optionally further with a computer or a cloud service.

Figure 2:
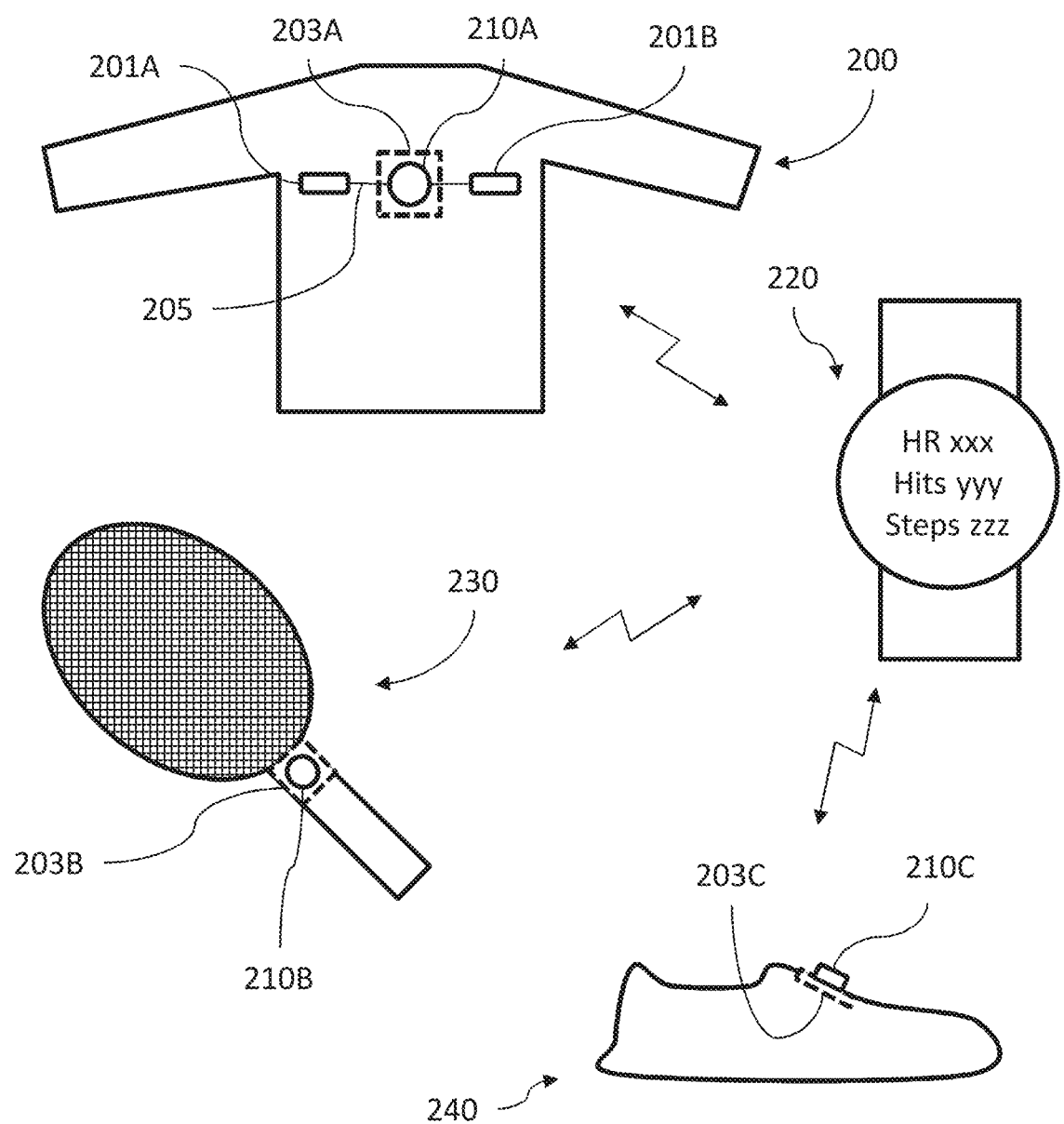
FIG. 2 shows another exemplary monitoring system with communication modules attached to garment with an integrated EMG sensor, tennis racket and shoe.

FIG. 2 shows an exemplary system with a sports garment 200 corresponding to the garment 100A of FIG. 1. The EMG pads are denoted with reference numerals 201A, 201B, the first mounting zone with 203A, wirings with 205 and the first communication module attached thereto with 210A. The mounting zone 203A comprises a respective identifier readable by the module 210A.

In addition, there is provided a tennis racket 230 with a second mounting zone 203B and a second communication module 210B and a sports shoe 240 with a third mounting zone 203C and a third communication module 210C. The mounting zones 203B, 203C of the racket 230 and shoe 240 may be connected to acceleration sensors, orientation sensors or position sensors, to mention some examples. The sensors deliver their corresponding acceleration, orientation and/or position information to the communication units 210A, 210B and 210C, and from these further to the monitoring unit 220. The mounting zones 203A, 203B and 203C may contain respective identifiers readable by the modules 210B, 210C to indicate what kind of operation of the communication modules 210A, 210B and 210C are required.

It is also possible that the racket 230 and/or shoe 240 are not provided with any sensors connected to the mounting zones 203B, 203C. In that case, their identifiers may "tell" the modules 210B, 210C that an internal sensor, such as an acceleration sensor, of the modules 210B, 210C are to be used. In this case, the identifiers can also be "void". In other words, if a module is not able to find any identifier with specific data content (identifier code), it assumes by default to operate in a particular way, typically using its internal sensor and corresponding pre-stored processing instructions for usage of the internal sensor.

The sports items 100A, 100B, 200, 230 and 240 may be passive, i.e., without a power source. In such cases the power for both identifier-reading and sensor operations is obtained from power sources contained in the communication modules 110A, 110B, 210A, 210B and 210C.

The present modules can be used in connection with any sports items within the personal-area network of a person. Examples are pieces of garment carried out by the person, such as shirts, trousers, socks, hats, caps, footwear, handwear and belts and various pieces of sports equipment necessary for any particular sports, including rackets, bats, clubs, sticks, skis, bicycles, balls, vehicles, and bags.

Examples of sensors contained in the sports items include the EMG, acceleration, orientation, position sensors already mentioned above, and additionally temperature and pressure sensors, such as air pressure sensors or tactile sensors, and photosensors. Specific sensor types for the abovementioned purposes include conductive electronic potential sensors, micromechanical acceleration sensors, micromechanical gyroscopic sensors, micromechanical magnetic sensors, micromechanical pressure sensors, satellite positioning system sensors (e.g. GPS or GLONASS) and resistive and capacitive touch sensors (with optional touch position and/or touch force detection capability) and digital imaging sensors (e.g. multipixel CCD or CMOS sensors).

Specific sports item examples include heartbeat ECG belts, muscular EMG belts or garments and tennis rackets, golf clubs, skiing equipment with acceleration sensors or orientation sensors and photographic devices used during the performance.

It should be also noted that the options discussed are not exclusive. Thus, the device carried by the sports item may be a combined sensor and actuator. The sensing and actuation functions typically relate to each other, but they need not do so. Sensor data analysis and actuator control can be carried out in suitable electronics of the sports item itself, but is even more preferably carried out in the present programmable communication module, which takes input from the sensor, processes the input and controls the actuator. In the first case, only power is minimally required from the communication module to the sensor/actuator. In the latter case, also data signals needs to be transferred between the module and the sensor/actuator, which is of course possible in the first case too. If no immediate response is required, part of data processing and/or actuation control may be carried out in the monitoring unit over a wireless channel.

An example of a combined device is an EMG sensor with built-in visual or audible output of EMG signal, EMG signal frequency or indication of target EMG activity rate (e.g.: in coaching mode: advice to increase or decrease heartbeat). Another example is a GPS sensor with built-in speed and/or direction indicator. A still another example is a racket, bat or club which comprises an acceleration sensor and/or gyroscope and is able to provide instant feedback for the user on the characteristics of a hit or swing.

Figure 3:
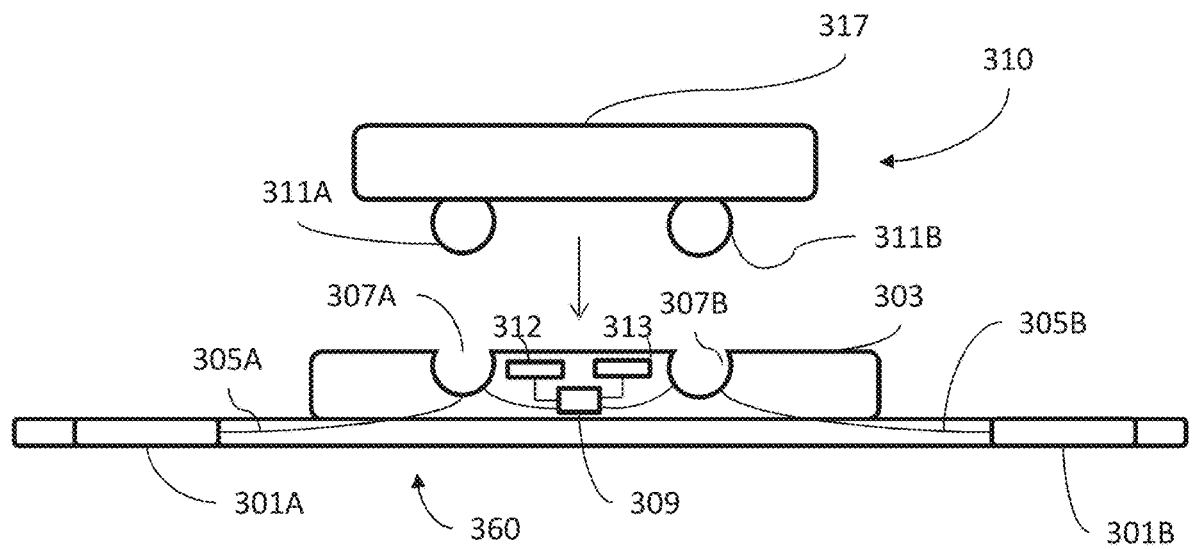
FIG. 3 shows a schematic side view of a communication module and mounting zone on a sports item.

FIG. 3 illustrates two key components of the system, the communication module 310 and sports item 360 in more detail. The communication module 310 comprises a housing 317 and two electric contact terminals 311A, 311B on outer surface of the housing. In this example, the contact terminals 311A, 311B are in the form of bumps or buttons capable of being snapped into suitable recess or female counterparts 307A, 307B of a mounting zone 303 of a sports item 360 to provide both attachment and electric connection. There may also be provided separate or additional means to take care of these functions.

In the mounting zone 303, there is provided a first processing unit 309 electrically connected to the recess counterparts 307A, 307B. Thus, when the module 310 is connected to the mounting zone 303, it is able to communicate with first processing unit 309 and to read sensor signals processed by unit 309. In this example, the recess counterparts 307A, 307B are additionally connected to EMG sensor pads 301A, 301B using suitable wirings 305A, 305B in the sports item 360 to provide an EMG signal to the module 310.

The first processing unit 309 may in some embodiments comprise a first memory unit 312 and interface circuitry 313. Obviously the memory unit 312 and or the interface circuitry 313 may be integral with the first processing unit 309, or separate components used by the processing unit. According to the invention, the first processing unit 309 is functionally connected to the mounting zone 303 and to sensors and/or actuators 301A, 301B, and is configured to process sensor signals from the sensors and/or actuators and to communicate with the communication module 310.

Further according to the invention, a remote device (not shown, see FIG. 5) is adapted to communicate with the communication module 310 over a wireless communication protocol in order to configure the communication module to process sensor or actuator signals from said sports item according to a use of the sports item. The use, e.g. a desired sport discipline, is selectable from a list containing a number of predefined uses in the remote device. A predefined code corresponding to the selected use may then be written into the first memory unit in order to configure and enable the mounting zone and the communication module to process sensor or actuator signals from the sports item according to a specific instruction set corresponding to the selected use of the sports item.

The predefined code my according to the invention be written into the first memory unit of the mounting zone 303 in at least two different ways. In some embodiments, the communication module 310 is configured receive the predefined code from the remote unit over the wireless communication protocol and to write the received predefined code into the first memory unit 312 in order to configure and enable the first processing unit and a second processing unit in the communication module 310 to process sensor or actuator signals from the sports item according to an instruction set corresponding to the selected use of the sports item.

It is to be noted that the location of the first memory unit is not restricted. According to some embodiments, the first memory unit 312 resides in the mounting zone 303 of the sports item 360 and is functionally connected to the first processing unit 309. However, the first memory unit may also reside in the communication module 310 being functionally connected both to the first and to the second processing unit (item 412 of FIG. 4). In fact, the first and second memory units may reside physically on the same circuit in the communication module.

Figure 5:
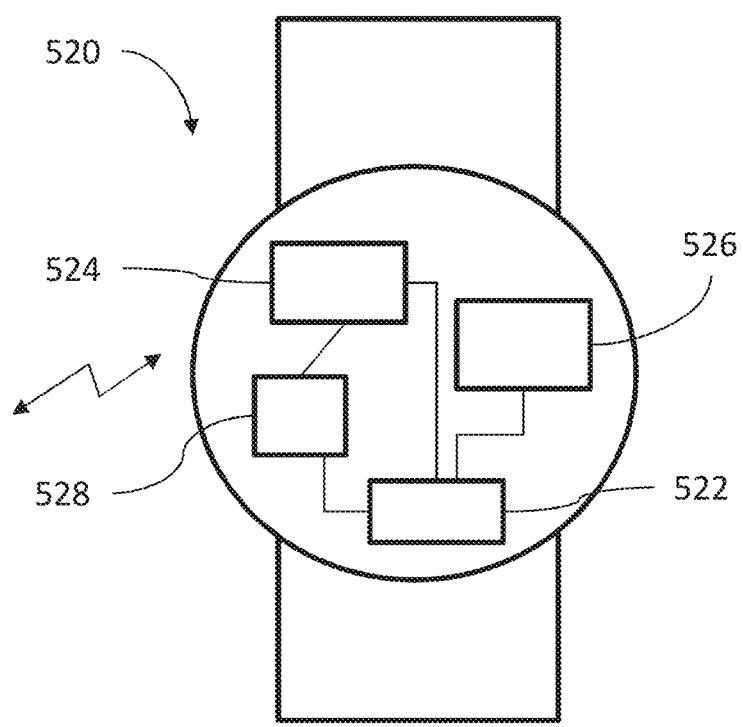
FIG. 5 illustrates a schematic block diagram of a monitoring unit according to one embodiment of the invention.

According to other embodiments, the a remote device of FIG. 5 is adapted to communicate directly with the interface circuitry 313 in the sports item over a near-field communication protocol in order to write the predefined code into the first memory unit 312. This will configure the sports item to process sensor or actuator signals together with the communication module according to a use of said sports item that is selected on the remote device and identified by the predefined code. In these embodiments, the interface circuitry 313 may comprise a radio-frequency identification (RFID) tag, such as a near-field communication (NFC) tag embedded in the mounting zone 303.

The communication module 310 may also contain a corresponding RFID/NFC read/write unit for reading RFID tags and to transfer information between the mounting zone 303 and the communication module over a near-field communication protocol via the tag 313. In such a case, the contact terminals of the module may serve for sensor signal reading only.

Figure 4:
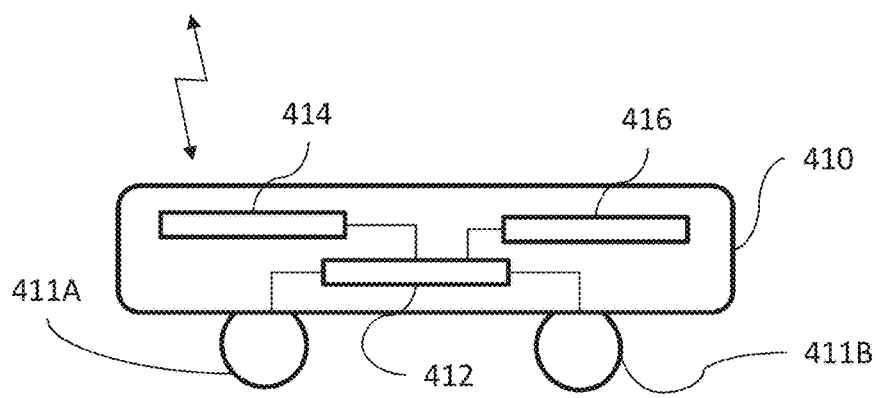
FIG. 4 shows a schematic block diagram of a communication module according to one embodiment of the invention.

FIG. 4 shows in more detail the main internal components of a communication module 410 according to one embodiment of the invention. The module 410 includes a second processing unit 412 configured to further process said sensor/actuator signals and to communicate processed signals to a remote device over a wireless communication protocol via a wireless communication unit 414. The contact terminals 411A, 411B connects the module 410 to a sports item 360 as is shown in FIG. 3. There may be provided a separate input and/or output unit (not shown) between the second processing unit 412 and the contact terminals 411A, 411B, the comprising conventional circuitry for amplification of input signals, if needed.

The processing unit 412 typically comprises a microcontroller operated by firmware, and a second memory unit 416 for storage of larger amounts of data, such as instruction sets. Tasks of the second processing unit 412 include performing internal data processing actions of the communication module 410, controlling communication to/from the monitoring unit and the sports item the module is attached to, and to perform configuration and execution of processing instruction sets selected on the basis of the predefined code delivered by the remote unit and read from the remote unit or the first memory unit 312 in sports item.

According to an important aspect of the invention, it is thus possible for the user to have several "generic" sports items, which are attachable on a variety of sport goods, such a s rackets, headbands, heart beat sensor belts, shoes etc. The predefined code that is retrieved for each use will configure the sports item and communications module to work according to an instruction set designed for that use. There is thus no need to manufacture and purchase separate sports items and modules for each use or sports discipline.

The contact terminals of the mounting zone described above may consists of female snaps 307A, 307B located on an mounting zone 303 that in turn is fastened on any suitable underlay or platform, such as a rubber band, suction cup, screws etc., in order to provide flexible attachment for the communications module suitable for any activity.

The communication unit 414 comprises an antenna and necessary electronics for amplification of the received and transmitted wireless signals and for coupling with the processing unit 412. The communication unit 414 can utilize any desired wireless communication protocol, and also include an integrated or separate RFID/NFC read/write unit for reading RFID tags. The wireless communication protocol is preferably a time slot-based protocol. Examples of suitable protocols include like Bluetooth LE and ANT+, using direct-sequence spread spectrum (DSSS) modulation techniques and an adaptive isochronous network configuration, respectively. A thorough description of the necessary hardware for various implementations is available e.g. from the Texas Instrument®'s handbook "Wireless Connectivity" which includes IC circuits and related hardware configurations for protocols working in sub-1- and 2.4-GHz frequency bands, such as ANT™, Bluetooth, Bluetooth low energy, RFID/NFC, PurePath™ Wireless audio, ZigBee®, IEEE 802.15.4, ZigBee RF4CE, 6LoWPAN, Wi-Fi®, GPS.

For example, in the case of Bluetooth LE, an Attribute Profile (ATT) wire application protocol is used. An attribute is composed of three elements:
 a 16-bit handle;
 an UUID which defines the attribute type;
 a value of a certain length.

A handle is a number that uniquely identifies an attribute and is expected to be stable for each device. A UUID (universally unique identifier) is an identifier standard used in software construction to enable distributed systems to uniquely identify information without significant central coordination. The value is an array of bytes of any size. The meaning of the value depends on the UUID.

Also TDMA-based protocols may be used, as discussed in "TDMA Protocol Requirements for Wireless Sensor Networks", Sensor Technologies and Applications, SENSORCOMM '08. Second International Conference on 25-31 Aug. 2008, Pages 30-35, ISBN: 978-0-7695-3330-8.

The module 414 is powered by a power source, typically a re-chargeable battery (not shown).

According to some embodiments, a complete instruction set that correspond to a certain code and an associated use of the device, is fetched from the remote device and stored in the second memory unit in the communication module. Alternatively, the instruction set may be generated from the code by an algorithm stored in the second memory unit in the communication module.

FIG. 5 depicts a remote device 520 in the form of a wrist-worn computer. Also the monitoring unit comprises a third processing unit 522 and a communication unit 524 for communication with one or more communication modules of the kind described above. There is also provided a memory unit 526 for storage of received/to-be-transmitted data.

The communication unit utilizes the same wireless communication protocol as the communication modules(s) it is intended to communicate with, as described above.

The remote device may equally well be a mobile handheld device, such as a smartphone. Such digital devices are usually equipped with all necessary hardware by default. What is then needed are applications running in the device, with which the configuration of various sports items and communication modules can be carried out.

A further task for a remote device capable of wireless communication may be to connect to external sources, e.g. over internet, to access identification codes and their associated instruction sets, updates etc. for downloading from a service provider.

In the other direction, training results and other personal data may be uploaded to such sites of service providers, for editing, displaying and/or sharing results and data in social media over e.g. internet.

A sports item to be configured may be an attachment and mounting zone for an oar, a racket or a band or the like for the wrist, head or shoulder etc. When the user of the remote device has selected the intended use of the sports item, the configuration starts by transferring the code for the selected use from the remote device to either the communications module by wireless transfer or to the sports item using an NFC communication protocol. The ID code is written into the first memory unit, and the second processing unit in the communication module activates, fetches or generates an instruction for the intended purpose. The instruction set may be partially or wholly tailored for a specific sport discipline, for the place on the body the sports item is fastened, and/or environmental parameters, such as running conditions (track/cross-country), indoor/outdoor activity etc.

One task of the processing unit 522 of the remote device 520 is to collect messages sent by communication units in the same personal-area network and to display and/or store relevant information form the messages to the user via a display or to the memory unit for further use. The processing unit picks form the messages data measured by the remote sensors and information on the time of the measurements and orders the measurement data in a chronological order in one or more data structures.

According to some embodiments of the invention, in an arrangement for configuring a sports equipment for personal performance monitoring and/or facilitation, the remote device adapted to communicate with the communication module over a wireless communication protocol and to send a predefined code to the communication module, in order to configure the same to process sensor or actuator signals from said sports item according to a use of the sports item as identified by the predefined code.

According to some other embodiments of the invention, in an arrangement for configuring a sports equipment for personal performance monitoring and/or facilitation, the remote device is adapted to communicate with a tag in the sports item over a near-field communication protocol, in order to write a predefined code into the first memory unit and to configure the sports item to process sensor or actuator signals from said sports item together with the communication module according to a use of the sports item as identified by the predefined code. At least in these embodiments, the remote device 520 is equipped with an integrated (in unit 524) or separate RFID/NFC read/write unit at least for the purpose of writing to an RFID tag embedded in the mounting zone 303, over a near-field radio communication protocol.

The monitoring unit 520 is powered by a power source 528, typically a re-chargeable battery.

Figure 6:
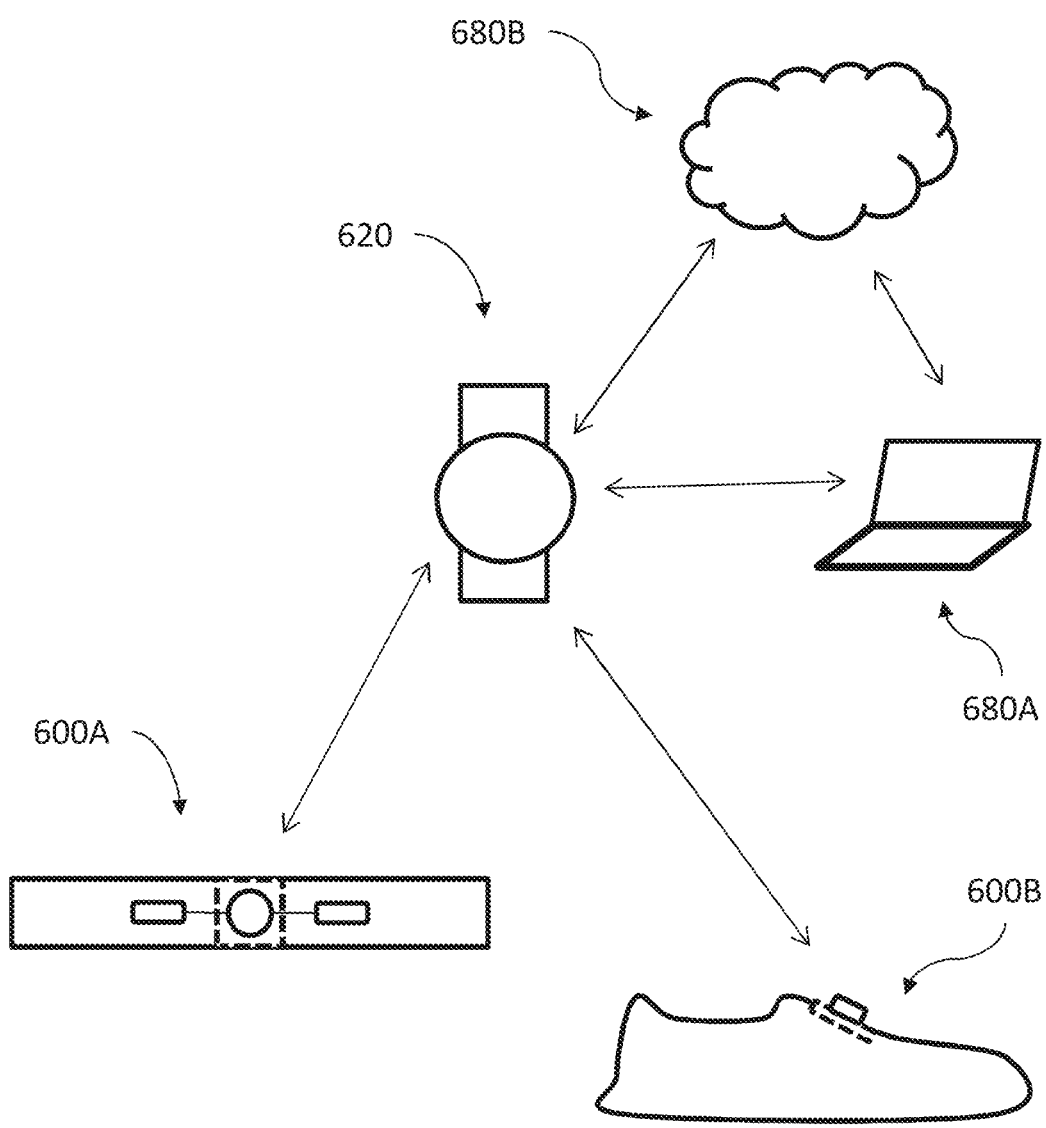
FIG. 6 illustrates a system extended from the monitoring unit to external devices or cloud services.

FIG. 6 shows an overview of a system which extends from a monitoring unit 620 to cloud services 680B over the internet and/or to an external computer 680A. The purpose of the system is to provide instruction sets to the communication modules of the sports items 600A, 600B connected to the system, as the communication modules themselves, but not necessarily either the remote unit does not contain instruction sets corresponding to the ID of the sports items. In such a case, the monitoring unit 620 may make a request for instruction sets to a computer 860A and/or a cloud service 680B. Connection from the remote unit to the internet cloud service 680B may be wireless, using e.g. the WLAN or mobile internet protocols. Connection to the computer 680A may be wireless or a cable connection.

The instruction sets are provided to the communication module as stand-alone applications, which can be run by the operating system (firmware) of the module. This allows for very generic modules still suitable for a variety of uses to be manufactured. Alternatively, the communication module may be able to generate instructions sets by means of a pre-stored algorithm for specific sports items based on the identification code of the sports item.

Figure 7:
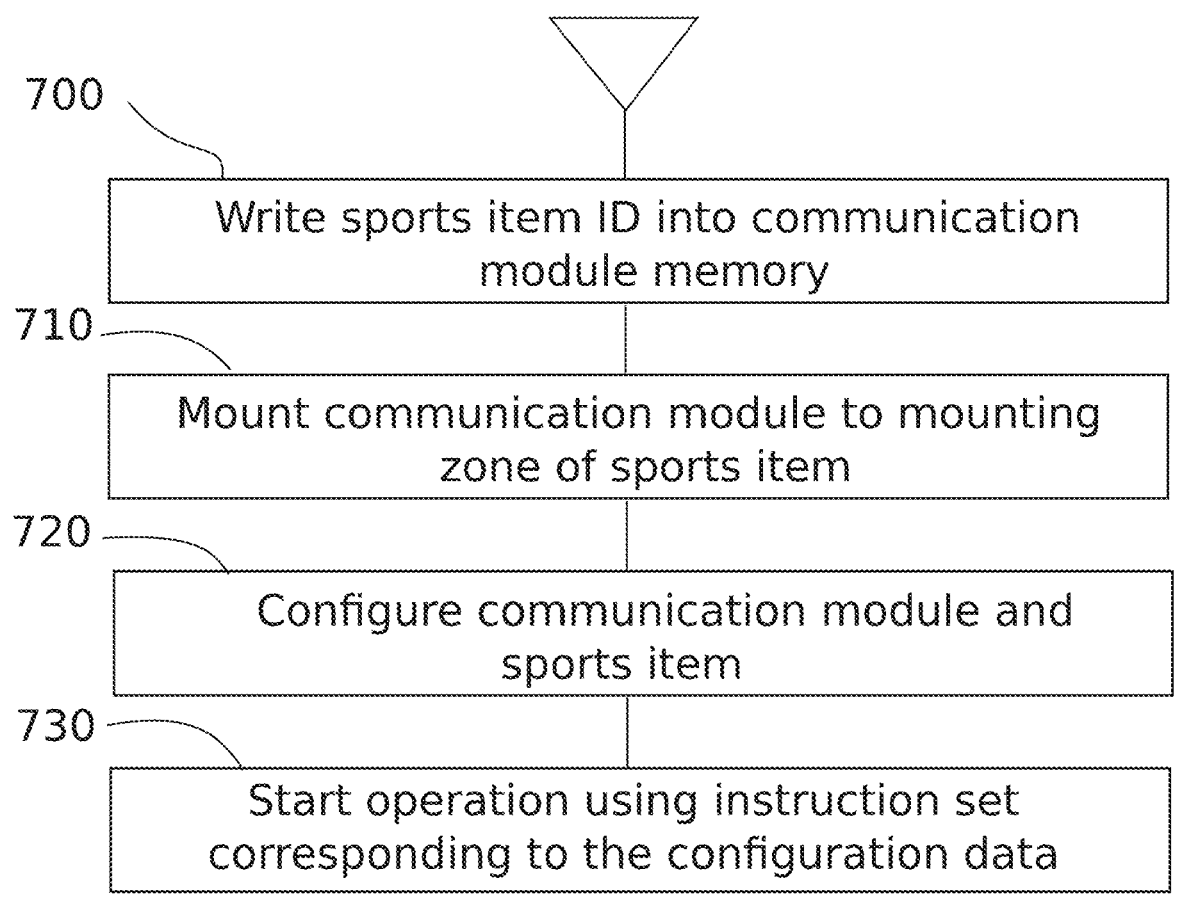
FIG. 7 shows a flow chart of one exemplary configuration method according to the invention.

FIG. 7 shows a flow chart of the present method according to one embodiment. First, in step 700, the sports item identifier is written from a remote device into the communication module memory (second memory unit). In step 710 the communication module is mounted to a mounting zone of a sports item designed to receive and hold the communication module thereon. The module makes electrical contact with the mounting zone via its contact terminals. It is to be noted that the mutual order of steps 700 and 710 is not critical. Next, in step 720, the identifier of the sports item is read by the communication module via the electrical contact and the configuration process is executed. Finally, in step 730, the instruction set is taken into use and the module adapts itself according to the instructions.

Figure 8:
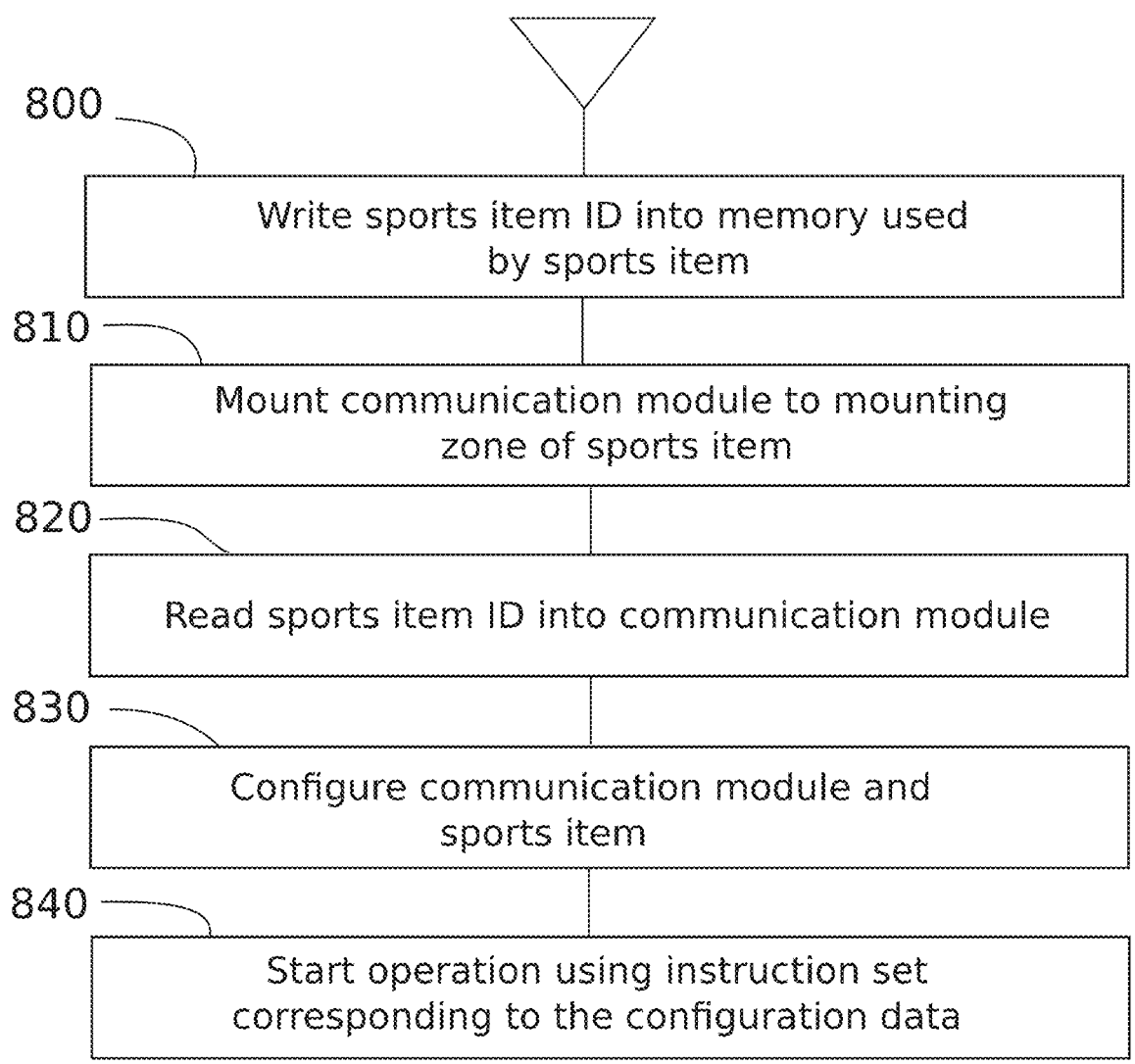
FIG. 8 shows a flow chart of another exemplary configuration method according to the invention.

FIG. 8 shows a flow chart of the present method according to another embodiment. First, in step 800, the sports item ID is written from a remote device into the first memory unit of the sports item. In step 810 the communication module is mounted to a mounting zone of a sports item designed to receive and hold the communication module thereon. The module makes electrical contact with the mounting zone via its contact terminals. It is to be noted that the mutual order of steps 800 and 810 is not critical. Next, in step 820, the identifier of the sorts item is read by the communication module via the electrical contact and in step 830 the configuration process is executed. Finally, in step 840, the instruction set is taken into use and the module adapts itself according to the instructions.

Figure 9:
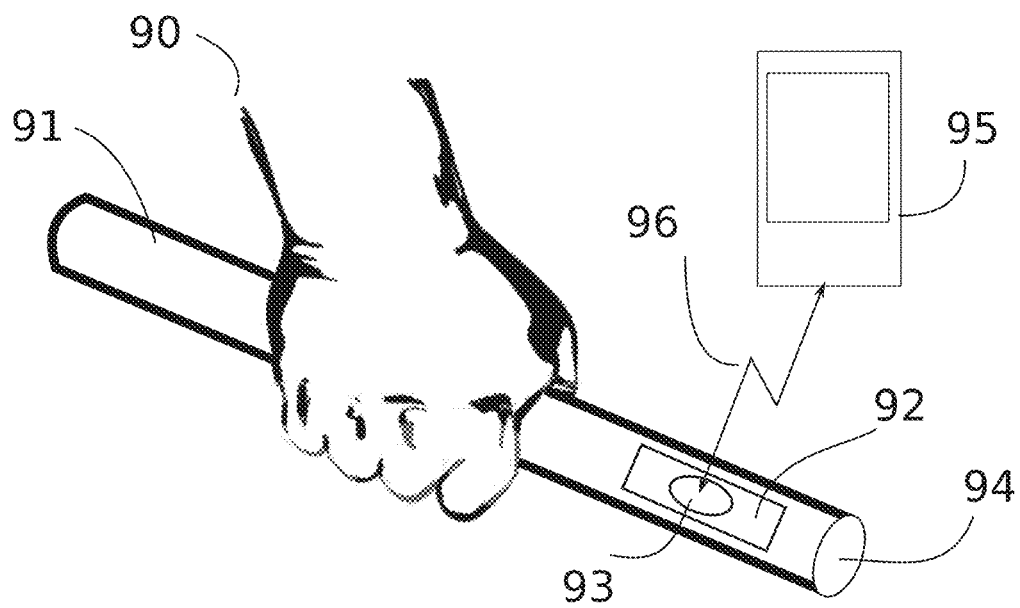
FIG. 9 illustrates a monitoring system according to one embodiment of the invention with communication modules attached to a tool with acceleration sensors.

FIG. 9 shows one example of a tool that can take advantage of the invention. A person is holding a tool in his hand 90. The tool is here shown as a generic one having a shaft 91 with a cut-off end 94. In the extension of the end 94 the head of an axe may be attached or the shaft may be the handheld portion of a welding pistol. On the shaft, a carrier item 92 is firmly attached, with glue, screws or otherwise. The carrier item comprises a mounting zone (not shown) for a communication module 93. When the person is working with the tool, actuators and/or acceleration sensors integrated in the carrier item 92 and/or the communication module 93 may register the status and/or the movements of the tool, and the communication module may then send raw sensor data, pre-processed sensor data, or analyzed tool performance data over a wireless link 96 to a remote device 95 for display and/or further processing. In this embodiment of the invention, the configuration of the carrier item 92 and the communication module 93 is made in the same way as described above. The predefined code identifying the tool is written by the remote device 95 to either a first memory of the carrier item 92 or sent to the communication module 93.

In the examples above, only sports items containing sensors functionally connectable with the communication module are discussed for simplicity. However, instead of or in addition to sensors, the carrier or sports items may contain actuators of any kind. An actuator differs from a sensor in that it produces a noticeable output for the user, whereas a sensor provides measurement information for the communication module to process and forward. The output may be visual, audible or mechanical (involving motion), for example.

Examples of actuators include an integrated display or audio output device in a garment. Another example is a tactile output device.

It should be noted that both sensors and actuators typically take the operating power from the communication module mounted to the sports item through suitable connectors and wirings.

The invention claimed is:

1. An arrangement for configuring equipment for personal performance monitoring, said equipment comprising:
   at least one carrier item comprising:
      one or more sensors and/or actuators,
      a tag comprising a near-field antenna and a first memory unit, and
      a mounting zone having a first processing unit functionally connected to said mounting zone, said sensors and/or actuators and said tag and arranged to process sensor signals from said sensors and/or actuators,
   at least one communication module having a second processing unit and adapted to be mounted on said mounting zone and to communicate with said first processing unit, said second processing unit being arranged to further process said sensor/actuator signals and to communicate processed signals over a wireless communication protocol, and
   a remote device adapted to receive said processed signals over said wireless communication protocol, wherein said remote device is further adapted to configure said carrier item by communicating a selected predefined code to said tag in said carrier item over a near-field communication protocol, in order to write said predefined code into said first memory unit and to said communication module over a wired connection from said first memory unit,
   whereby said personal performance monitoring by processing sensor or actuator signals with the first processing unit and further processing said sensor or actuator signals with the second processing unit is performed according to a configured use of said carrier item as identified by said predefined code.

2. An arrangement according to claim 1, wherein the carrier item is configurable by said predefined code to enable said first and second processing units to process sensor or actuator signals from said carrier item according to an instruction set corresponding to said configured use of said carrier item.

3. An arrangement according to claim 2, wherein said instruction set is fetched from said remote device and stored in a second memory unit in said communication module.

4. An arrangement according to claim 2, wherein said instruction set is generated from said predefined code by an algorithm stored in a second memory unit in said communication module.

5. An arrangement according to claim 1, wherein a carrier items comprise a belt, a garment and/or a piece of sports equipment, such as a bat, racket, club, ski or bicycle, with one or more integrated sensors or actuators.

6. The arrangement according to claim 1, wherein said mounting zone for said communication module comprise conductive fasteners such as snaps located on an outer surface of a housing for said communication module, in order to secure the communication module to the mounting zone and for providing electronic contact terminals for communication between said carrier item and said communication module.

7. The arrangement according to claim 1, wherein the remote device have access to a plurality of instructions sets corresponding to different predefined uses of said carrier item.

8. The arrangement according to claim 1, wherein said tag in said carrier item comprises a radio-frequency identification (RFID) unit.

9. The arrangement according to claim 1, wherein the sensors or actuators are EMG sensors, acceleration sensors, power sensors, speed sensors, a satellite positioning sensor or a trigger actuator for a trigger or drive signal.

10. A method for configuring equipment for use in personal performance monitoring, comprising the steps of:
   providing at least one carrier item having functionally connected thereto sensor and/or actuators, a tag comprising a near-field antenna and a first memory unit, and a mounting zone having a first processing unit arranged to process sensor signals from said sensors and/or actuators,
   providing in said mounting zone at least one communication module having a second processing unit being arranged to further process signals from said sensors and/or actuators and to communicate processed signals over a wireless communication protocol,
   a remote device capable of wireless communication with said communication module over the wireless communication protocol,
   wherein said remote device is further adapted to configure said carrier item by:
   communicating a selected predefined code from said remote device over a near-field communication protocol to said first memory unit in said tag, configuring said communication module over a wired connection from said first memory unit to facilitate personal performance monitoring by processing sensor or actuator signals from said carrier item with the first processing unit and further processing said sensor or actuator signals with the second processing unit according to a use of said carrier item as identified by said predefined code.

11. A method according to claim 10, wherein the carrier item is configured to enable said first and second processing units to process sensor or actuator signals from said carrier item according to an instruction set corresponding to said use of said carrier item.

12. A method according to claim 11, wherein said instruction set is fetched from said remote device and stored in a second memory unit in said communication module.

13. A method according to claim 11, wherein said instruction set is generated from said predefined code by an algorithm stored in a second memory unit in said communication module.

14. A method according to claim 10 for configuring sports equipment in order to monitor personal performance in sports.

15. A method according to according to claim 10 for configuring a tool in order to monitor personal performance when working with such tool.

16. The use of an arrangement according to claim 1 for configuring sports equipment in order to monitor personal performance in sports.

17. The use of an arrangement according to claim 1 for configuring a tool in order to monitor personal performance when working with such tool.

18. The arrangement according to claim 1 wherein at least one of the processing or further processing is performed using processing instructions selected at least in part based on the configured use of said carrier item as identified by said predefined code.

19. A method according to claim 10 wherein at least one of the processing or further processing is performed using processing instructions selected at least in part based on the configured use of said carrier item as identified by said predefined code.

* * * * *